United States Patent [19]

Huergo et al.

[11] Patent Number: 5,747,653
[45] Date of Patent: May 5, 1998

[54] METHOD OF PRODUCING OF AN ANTIMENINGOCOCCIC HYPERIMMUNE GAMMA GLOBULIN AND GAMMA GLOBULIN PRODUCED BY METHOD

[75] Inventors: Concepción Campa Huergo, Havana City; Victoriano Gustavo Sierra Gonzalez, Villa Clara; Maria Mercedes Gutiérrez Vazcuez, Hauana; Gonzalo Bisset Jorrin, Havana City; Luis Guillermo Garcia Imia, Havana City; Gisela de la Caridad Puentes Rizo, Havana City; Maria del Carmen Sampedro Herrera, Havana City; Franklin Sotolongo Padrón, Havana City; Eloisa Xochitl Le Riverend Morales, Havana City; Manuel Alfredo Galguera Dominguez, Villa Clara, all of Cuba

[73] Assignee: Centro Nacional De Biopreparados, Havana City, Cuba

[21] Appl. No.: 692,055

[22] Filed: Aug. 2, 1996

Related U.S. Application Data

[62] Division of Ser. No. 152,938, Nov. 12, 1993, Pat. No. 5,597,572, which is a continuation of Ser. No. 767,341, Sep. 27, 1991, abandoned, which is a continuation of Ser. No. 225,859, Jul. 29, 1988, abandoned.

[30] Foreign Application Priority Data

Jul. 30, 1987 [CU] Cuba .......................... 125/87

[51] Int. Cl.$^6$ .......................... C07K 16/12; A61K 39/40; A61K 39/095; A23J 3/20

[52] U.S. Cl. .......................... 530/389.5; 530/412; 530/413; 530/414; 530/415; 530/416; 530/417; 530/418; 530/419; 530/427; 530/387.1; 424/130.1; 424/197.11; 424/250.1; 424/278.1; 424/279.1; 424/282.1; 424/531

[58] Field of Search .......................... 424/134.1, 164.1, 424/197.11, 250.1, 278.1, 279.1, 282.1, 130.1, 531; 530/412, 413, 387.1, 414, 415, 416, 417, 418, 419, 427, 389.5

[56] References Cited

U.S. PATENT DOCUMENTS

| | | |
|---|---|---|
| 4,451,446 | 5/1984 | Vandevelde et al. . |
| 4,505,853 | 3/1985 | Goldstein et al. . |
| 4,601,903 | 7/1986 | Frasch . |
| 4,629,723 | 12/1986 | Goldstein et al. . |

OTHER PUBLICATIONS

Sigma Catalog, published by Sigma Chemical Company (St. Louis, MO), see p. 1192 1988.

*Primary Examiner*—Anthony C. Caputa
*Attorney, Agent, or Firm*—Lackenbach Siegel Marzullo Aronson & Greenspan, PC

[57] ABSTRACT

A vaccine effective against infection caused by group B *Nesseria meningitidis* microorganism is provided which comprises a purified protein antigenic complex weighing from 65 to 95 kDa, vesicles, and capsular polysaccharides. This vaccine is extracted from the cell membranes of the live microorganisms using detergent and enzyme. The method of producing an antimeningococcic hyperimmune gammaglobulin and the gammaglobulin produced by the method was provided. The gammaglobulin is obtained from vaccinees vaccinated with the vaccine.

10 Claims, 1 Drawing Sheet

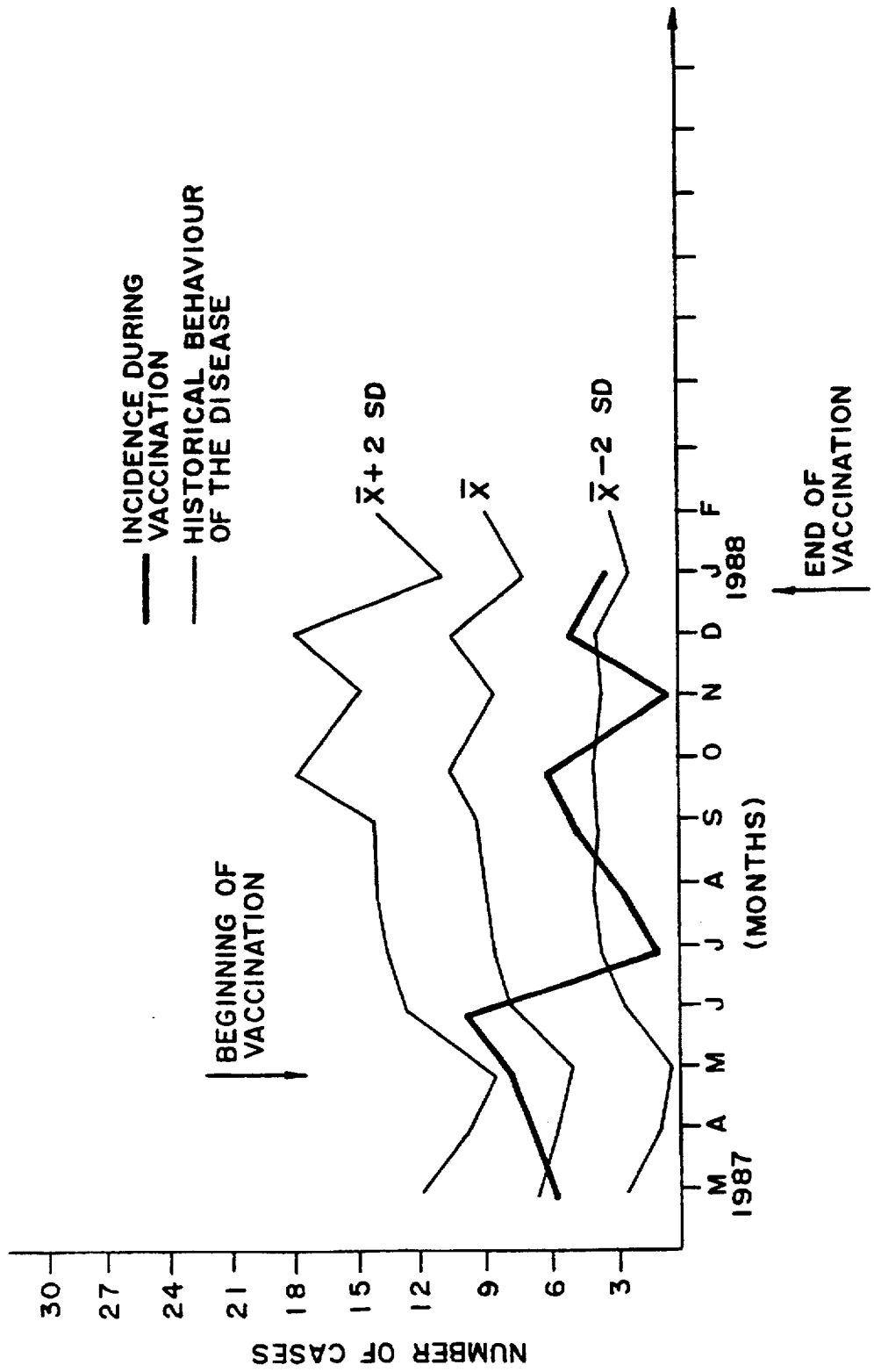

METHOD OF PRODUCING OF AN ANTIMENINGOCOCCIC HYPERIMMUNE GAMMA GLOBULIN AND GAMMA GLOBULIN PRODUCED BY METHOD

This application is a division of application Ser. No. 08/152,938, filed Nov.12, 1993, now U.S. Pat. No. 5,597, 572, issued Jan. 28, 1997, which is a continuation of application Ser. No. 07/767,341, filed Sep. 27, 1991, abandoned, which is a continuation of application Ser. No. 07/225,859, filed Jul. 29, 1988, abandoned.

FIELD OF THE INVENTION

The present invention is related with the field of medicine and more particularly with the prophylaxis and treatment of diseases caused by pathogenic bacteria.

OBJECTS OF THE INVENTION

The object of this invention is to provide a method for obtaining a vaccine against the different pathogenic serotypes of group B *Neisseria meningitidis*, and also the resulting vaccine.

Another object of the present invention is to provide a process for the preparation of antimeningococcic hyperimmune gammaglobulin.

An additional aim of the present invention is a method for obtaining a specific transfer factor (dialyzable factor in leukocyte extracts) which may be employed for conferring T-cell immunity against *Neisseria meningitidis* B and its transfer factor.

BACKGROUND OF THE INVENTION

*Neisseria meningitidis* has the typical envelope of Gram-negative bacteria, consisting of a cytoplasmic membrane, a peptidoglycan layer and an outer membrane with three layers, which, together with the capsular polysaccharide, constitute the bacterial wall.

From an immunological point of view, those structures which may interact with the immune system in any of the stages of the microorganism-host relationship and especially the first stages, i.e., the most external components, are of greater importance. Classification of this microorganism has been made on the basis of groups, types and subtypes, through techniques utilizing polyclonal (Frasch, C. E. and Chapman, 1973 , *J. Infect. Dis* . 127: 149–154) or monoclonal antibodies (Hussein, A., *Monoclonal Antibodies and N. meningitidis. Proefschrift*. Utrecht, Nederland, 1988).

Nowadays 12 serogroups are known: A, B, C, X, Y, Z, 29-E, W-135, H, I, K, and L (Ashton, F. E. et al., 1938, *J. Clin. Microbiol.* 17: 722–727; Branham, S. E., 1956, *Can. J. Microbiol.* 2: 175–188; Evans, A. C., 1920, *Lab. Bull.* 1245: 43–87; Shao-Qing, et al., 1972, *J. Biol. Stand.* 9: 307–315; Slaterus, K. W., 1961, *Ant. v. Leeuwenhoek J. Microbiol. Serol.* 29: 265–271). Such groups have been differentiated according to the capsular polysaccharide (CPS) which vary among each of these groups in certain antigenic determinants (Branham, S. E.,1940, *Bacteriol. Rev.* 4: 59–96; Frasch, C. E. et al, 1985, *Rev. Infect. Dis.* 7: 504–510).

In spite of variations in epidemiology in different regions of the world and a lack of adequate systems of sanitary control in some countries, it has been possible to establish that, among all these groups, at present only groups A, B, C, Y, and W-135 are responsible for more than 90% of the meningitidis cases in the world (Abdillahi, H., 1988, Proefschrift, pg. 13 Utrecht, Nederland). Other authors ascribe more than 95% (Frasch, C. E. *Eur. J. Microbiol.* 4: 533–536) of cases to these five The capsular polysaccharides, purified and characterized, and used so far as vaccines have proved efficient enough to control the outbreaks and epidemics of the groups A, C, Y, and W-135, as mono-, di, tri, or tetravalent vaccines (Gold et al., 1969–1970, *Bull. WHO* 45: 272–282; Gotschlich et al., 1969, *J. Exp. Med.* 129: 134–136; Hankins, 1982, *Proc. Soc. Biol. Med.* 169: 54–57). In spite of deficiencies still to be solved such as: poor or no-response to polysaccharide C in children under 2 years of age; thermalability of polysaccharide A; difficulties regarding the induction of tolerance after re-vaccination with polysaccharides A and C, to the point that in some places increase of meningitidis cases has been detected (Marzochi, K. B. F., Meningitidis Meninigococcica. Tese (doutorado) Universidade Federal do Rio de Janeiro, Brazil (328 pg.), 1985). Now the polysaccharide vaccines are an effective enough weapon in the struggle against disease caused by groups A, C, Y, and W-135, but not against group B, the capsular polysaccharide of which is a very poor immunogen (Wyle et al., 1972, *J. Infect. Dis.* 126, 514–522; Zollinger, et al., 1979, *J. Clin. Invest.* 63: 836–834; Jennings et al., 1981, *J. Immunol.* 127: 104–108). It may be due to different causes such as the cross reactivity with antigens of the host itself (brain sialoglycopeptides), conformational changes suffered by these polysaccharides when they are purified, and their great sensitivity to enzymatic and other types of degradation occurring in the organism, such as rapid esterification, etc. (Lifely, M. R. and Moreno, C., 1986, *Lancet*, Jan. 25, 214–215). The final result is that, despite the intense work of important researchers and companies, such as the Wellcome Foundation, it has been impossible until now to produce from the group B polysaccharide a satisfactory immunogen. Because of these reasons, the general methods for vaccines from the other polysaccharide groups used for vaccines do not work for group B. Because serogroup B is today the main cause of the meningococcal disease in most temperate counties, as well as other regions throughout the world, it is desirable to obtain alternative vaccines. Every attempt at finding these alternative vaccines should therefore be based upon non-capsular antigens, especially those in the outer membrane, taking into account their significance in the microorganism-host relationship.

Almost every research group has focused its attention on the proteins, since the other relevant components would be the lipopolysaccharides (LPS), but their highly toxic nature, their high pyrogenic activity and their mitogenic capacity have prevented considering this element as a vaccine option, although it is the most important in the pathogenesis of the meningococcal disease.

The principal proteins in the outer membrane, both from groups B and C give rise to subdivisions of these groups in serotypes (from now on we shall only refer to group B). They are based on the immunologic specificity of these principal proteins detected in reactions with polyclonal and monoclonal antibodies in different techniques (Abdillahi, H. *Proefschrift*. Utrecht, Nederland, 1988). Group B has already been subdivided into more than 18 serotypes.

Preferred techniques include double immunodiffusion, counterimmunoelectrophoresis, radioimmunoassay, ELISA, SPRIA, coagglutination using protein A coated Staphylococcus aureus to fix monoclonal antibodies or other solid carriers, agglutination by latex, etc. (Gold, R. and Wyle, F. A., 1970, 1: 479–484; Jones, O. M. and Tobin, B. M., 1976, *J. Clin. Pathol.*29: 746–748; Zollinger, W. D. and Mandrell, R. E., 1977, *Infect. Immun.* 5: 98–102; Frasch, C. E. and Chapman, S. S., 1973, *Infect. Dis.* 127: 149–154; Danielsson, D. and Olsen, 1979, *J. Clin. Pathol.* 32: 136–142).

With the aid of monoclonal antibodies it has even been possible to subdivide further different serotypes correlating them with their degree of "virulence", e.g. serotype 2 was subdivided into 2a, 2b and 2c (Abdillahi, H. and Poolman, J. T.,1988, *Proefschrift*. Ch. 6 pg. 69–78, Utrecht, Nederland; Poolman, J. T. et al., 1980, *J. Gen. Microbiol.* 116: 465–473).

It is obvious that, by using the principal proteins of the outer membrane as a basis for the immunogen, we are preparing a specific serotype immunogen. In spite of the fact that it has been found that among all the serotypes only a few are disease agents (Frasch, C. E., et al, 1972, *Seminars in Infectious Diseases*, Vol. 1, S.I.M. Book Corp., N.Y. 304–337) while others seldom are, it would be impossible to prepare an immunogen based on a serotype, which would have sufficient antigenic determinants for all the serotypes causing disease. Therefore, serotype vaccines as such have a small range of effectiveness, aiming only at the specific serotype with which the vaccine was elaborated. This has been the history of almost all the protein vaccines prepared in the last few years and that has been among several others, one of their major limitations. Vaccines based on serotype 2a proteins have been prepared from vesicles of the outer membrane (Frasch, C. E. et al., 1982, *Infect. Immun.* 37: 271–280) and certain variants of those vaccines have been studied regarding their immunogenicity and toxicity in animals (Peppler et al., 1982, *Infect. Immun.* 37: 264–270) and assessed for their safety and immunogenicity in voluntary adults (Frasch, C. E. et al., 1982, *Sem. Infect. Dis.* 4; Zollinger et al, 1979, *J. Clin. Invest.* 63: 836–848).

Other research work also reveals the importance of the solubility of these vaccines (Frasch, C. E. et al., 1982, *Sem. Infect. Dis.*, 4; Frasch, C. E., 1978, *J. Exp. Med.* 147: 629–644).

The benefits of the use of capsular polysaccharides and different adjuvants of aluminum hydroxide or phosphate have also been reported by numerous authors (Frasch, C. E., 1983, *Med. Microbiol.* Vol. 2 Acad. Press, N.Y.). In some cases a careful study has been carried out on the correlations among the proportions of those components, their electron microscopy picture and their response in different animals, including primates and humans of different age groups (Campa, C. et al, 1986).

In our research work we even found the solution for the lack of immunogenicity in children under 2 years of age.

SUMMARY OF THE INVENTION

The present invention provides a method for producing a vaccine against different pathogenic serotypes of group B *Neisseria meningitidis*, whose main novelty is based on the use of a protein antigenic complex of high molecular weight common to all pathogenic serotypes, which anchored in the vesicles of the outer membrane of the microorganism, constituted, among other components, by serotype majority proteins of the strain used in the production and the whole adjuvated, permits the obtainment of a protective preparation never before attained.

The vesicles constitute one of the elements of the vaccine that contribute antigenic determinants of the antigenic majority proteins. They regulate immunologically LPS and constitute the ideal structure for anchorage of other proteins, which are in minority in the B meningococcus, but that are common to all the pathogenic types tested and very good immunogens, that induce long-lasting bactericidal response.

The wide range common protective character is conferred by the antigenic community in group B in the zone of the high molecular weight protein antigenic complex. The high molecular weight protein antigenic complex also "adjuvates" and increases the response against other antigens, besides being responsible for the prolonged immunologic memory.

The serotype antigens are important in the first stage of the protective response (4–6 months), but afterwards the protective titer is mainly detected against the high molecular weight protein antigenic complex.

For this reason the second component of our vaccine is the protein antigenic complex of 65–95 kD molecular weight, which is added to the vesicles in a proportion of 15% ±3.

The vesicles by themselves would probably serve as a serotype vaccine of moderate and transitory effectiveness.

Another novelty of the method is the extraction of the proteins of the outer membrane by combined treatment of live microorganisms with detergent, enzyme and ultrasonic bath, and more specifically using sodium deoxycholate, sodium dodecyl sulphate and BRIJ-96 (polyoxyethylene 10 oleyl ether) as detergents at the following respective concentrations: lower than 1%, from 0.1–5%, and from 0.01–0.05%, all are independently combined with lysozyme at a concentration of 0.03–1% and ultrasonic bath. A variant of this process of extraction consists in using TWEEN 80 (sorbitan monooleate polyoxyethylene) combined with ultrasonic bath. Examples of membrane protein extractive media.

| EXTRACTIVE MEDIA | YIELD | Contam.DNA |
|---|---|---|
| DOC 0.1–2% | 2–3 mg/g | 20% |
| DOC less than 0.1% + lysozyme 0.03–1% + US | 2–3 mg/g | 20% |
| TWEEN 80 0.1–2% | 1.2–2 mg/g | 15% |
| SDS 0.1–0.5% + lysozyme 0.03–1% + US | 1.8–3.2 mg/g | 22% |
| BRIJ 96 0.1–0.5% + lysozyme 0.03–1% + US | 1.5–2.1 mg/g | 12% |

US: ultrasonic bath

Contaminant DNA refer to the % of the total of DNA/total protein which must be eliminated in the subsequent steps. The extraction process of membrane proteins is carried out at a temperature between 2°–10° C., with an extraction time between 5 minutes and 5 hours with magnetic or mechanical (250–950 rpm) stirring; the medium in which extraction takes place may be constituted by different aqueous buffers. The pH is maintained between 6.5–9.0 depending on the extractive combination used; magnetic or mechanical stirring can be alternated with ultrasonic treatment.

The novel procedure for purifying the protein extract by a dissociative treatment with detergent, ultrasonic treatment and chromatography, after the elimination of nucleic acids. With this combination the modulation of the content of LPS, phospholipids, and other lipids of the vesicles, which provides the vaccine with the capacity to induce an effective antibody response against endotoxin. One may use as detergent sodium deoxycholate, BRIJ-96, TWEEN 20 (sorbitan monolaurate polyoxyethylene), TWEEN 80 in a concentration of 0.1–6%. The molecular sieving is carried out in a SEPHACRYL S-300 (cross-linked copolymer of allyl dextran and N,N'-methylenebisacrylamide used for gel filtration and fractionation of globular proteins with a molecular weight of 10,000 to 1.5 million) and S-400 (cross-linked copolymer of allyl dextran and N,N'- methylenebisacrylamide used for gel formation and fractionation of globular proteins with a molecular weight of 20,000 to 8 million) or SEPHAROSE CL-4B column composed of crossed-linked beaded agarose for fractionation of globular proteins with a molecular weight of 60,000 to 20 million.

It is still another novel characteristic of the method object of the present invention, to purify the antigenic material, resulting from the modulation by employing high molecular weight protein antigenic complex of 65–95 kD molecular weight, using high performance liquid chromatography (HPLC) (TSK3000 SW6 column), or affinity chromatography with monoclonal antibodies or hydrophobic chromatography or ionic exchange chromatography or a combination of any of these.

It is an essential feature of this method that it adds to the fraction containing the vesicles of the protein antigenic complex in a proportion of 15%±3 using ultrasonic treatment so that the complex is anchored on them.

With ultrasonic treatment integration of the antigenic complex is facilitated onto the vesicles naturally formed and that already possess traces of those proteins as leftover from purification; in this way the vesicle works as a carrier or adjuvant with respect to that antigen of high molecular weight.

To the fraction containing the vesicles, capsular polysaccharide is added in a proportion of 1:1–1:4 with respect to protein and adjuvant in a proportion of 20°–100° mcg/mcg of protein. As adjuvant aluminum hydroxide, aluminum phosphate or calcium phosphate are preferred.

By adding the aforementioned proportions of capsular polysaccharide and adjuvant one obtains an increase in the immunogenicity of the vaccine preparation. Also an adequate presentation of the lipopolysaccharide component reduces capacity to induce undesirable reactions to a minimal level.

The different components of the vaccine mixture are radiation sterilized by ionizing cobalt 60 radiations, with 5–25 Kilogray (kGy) doses, at a temperature from 1°–4° C. before preparing the final mixture or sterilization may be carried out by this procedure once the resulting mixture is obtained. The use of ionizing radiation for sterilization of the individual components of the vaccine mixture or jointly, in liquid or lyophilized form or to modify the immunogenicity is described for the first time for this type of vaccines.

It is a variant of the present invention, to sterilize the components by membrane filtration.

One may use both procedures in combination: cobalt 60 ionizing radiation at mentioned doses and temperatures and membrane filtration, in such a way that some of the components are sterilized by the first procedure independently and the rest by the second described procedure.

BRIEF DESCRIPTION OF THE DRAWING

The novel process of the invention produces a novel vaccine against Neisseria meningitidis B pathogens of the SB type. The FIGURE graphically depicts the historical and present behavior of the meningodisease at the site of the field trial. 142,000 volunteers ranging in age from 6 months to 24 years of age were vaccinated. The legend of the FIGURE states that the heavy line graph depicts the incidence during vaccination and the lighter line graphs depict the historical behavior of the disease. The number of cases was plotted against the period of time from the beginning of vaccinations in 1987 to the end of vaccinations in 1988.

DETAILED DESCRIPTION OF THE INVENTION

The vaccine obtained by the described method of the invention possesses a wide long-lasting protective range against the various pathogenic serotypes of group B Neisseria meningitidis. It is the first vaccine against B meningococci to reach the level of mass efficacy field trial, having already reached a total of 300,000 volunteers.

This vaccine contains an immunologically effective quantity of the protein antigenic complex or molecular weight 65–95 kD, which confers antigenic community for the different pathogenic serotypes and induces the production of bacteriocidal antibodies. It also contains a quantity of vesicles in the necessary proportion to induce a strong antibody response against the serotype antigenic determinants and the endotoxin. A proportion of capsular polysaccharide increases the solubility and immunogenicity of the whole, which at the same time increases the response of the organism to the polysaccharide component, even for children under 2 years of age and defines its polyvalent property. The vaccine is optimized by the necessary quantity of adjuvant.

The invention also permits one to obtain, from blood donations of the vaccinees, a hyperimmune antimeningococcic gammaglobulin preparation used successfully for the first time in the prophylaxis and treatment of meningitis and meningococcemia caused by any of the various pathogenic serotypes of group B Neisseria meningitidis against which it possesses bacteriocidal and neutralizing activity.

The invention also provides for the first time, a specific transfer factor (dialyzable factor from donor's white blood cells), which is capable of transferring T-cell immunity against this microorganism.

Controls.

The controls of polysaccharide C are established by the standards of the WHO and they are strictly met. The controls for the protein preparations are:

Electrophoresis in polyacrylamide gel. (Tsai and Frasch, 1980, J. Bacteriol. 141: 169–176). In the electrophoretic patterns obtained, besides the serotype majority proteins, 12–15% proteins of the antigenic complex with high molecular weight 65-95 kD are found.

KDO. (Osborn, et al., 1963, Proc. Natl. Acad. Sci. USA 50: 499–506). In the variant studied up to yield level the permissible limit established was 10%. Other variants with KDO over 10% are now being studied in human volunteers.

Nucleic acids. After eliminating protein with extensive phenol and dialysis, differential spectrophotometric reading (260–280 nm) is carried out so as to verify detectable absence of proteins and then the nucleic acid concentration is calculated by light adsorption at 260 nm, where the extraction coefficient E (0.1%, 1 cm)=20.0.

Sialic acid. The residual polysaccharide B content was measured according to the method of L Svennerholm (Biochem. Biophys. Proc. 24: 604, 1957). In our variant, conducted up to the field trial level, a 1–10% limit was established.

Electron microscopy. It is carried out as a routine procedure as described by Frasch and Peppler (Infect. Immun. 37: 271–280, 1982). The ultra-microscopic image is correlated with solubility and immunogenicity. Other structural studies are under way with the variants under study. The protein concentration was determined by the Lowry method (1951. J. Biol. Chem. 192: 265–275).

Final vaccine controls.

Information stated below refer to the variant of our vaccine which is undergoing field trial in human subjects.

Composition. Protein antigens: 100±20 mcg per ml. Polysaccharide: 100±20 mcg per ml. Aluminum hydroxide (gel) 4 mg per ml. Thimerosal: 1 g in 10,000 ml. The dose is 0.5 ml.

Thimerosal. (merthiolate, sodium-ethyl-mercurithisalicylate). Is determined by spectrophotometry using diphenyl-thiocarbzone, according to WHO *Manual*BLG/UNDP/77.1 Rev. 1 pp 84–85. Permissible limits range from 0.005 to 0.02% pH measurement. Using a pH meter with glass and calomel electrode and standard buffer solutions (BDH) at pH values 5.0, 7.0, 9.0. Allowed pH values must be in the range of 7.0±0.4.

Determination of aluminum content. It is performed according to Appendix D. 18 of booklet WHO/UNDP/77.1 Rev. 1 pp 87–88. The criterion of acceptability is not to exceed 1.25 mg Al (aluminum) per dose.

Determination of antigen concentrations and percent of absorption to adjuvant gel.

The absorbed vaccine is centrifuging and concentrations of protein and polysaccharides in the supernatant and sediment are determined using the above mentioned methods. The preparation is accepted if not over 20% of total antigens originally added are free in the supernatant.

Sterility control. It is performed according to specifications in Appendix D.27 of BLG/UNDP/77.1 Rev. 1, *General Requirements for the Sterility of Biological Substances* and the corresponding Cuban standards.

Innocuousness control. Every batch is tested for innocuousness by giving a human dose (max. 1 ml) to 5 adult mice weighing 17–22 g and not more than 15 ml to 2 guinea pigs weighing 250–350 g. The preparation is accepted if no animal shows ill health during 7 days following inoculation. If anyone of the animals dies or shows ill health and the others are not affected, the test is repeated. The batch is approved if none of the animals in the second group dies or shows ill health after 7 days. Electron microscopy. Samples of final vaccine batches are subjected to electron microscopy using the method already mentioned.

ELISA. The solid phase immunoenzymatic assay was performed as described by Peppler and Frasch (*Infect. Immun.* 37: 264–270,1982), and adapted to our antigen's coupling characteristics, mostly in order to have a reference system for our method. This system is based on the use of PVC ultra-microplates with wells covered by polystyrene, and 10 ml effective volume capacity, which are read in the equipment (SUMA) developed at the Centro de immunoensayo (Habana, Cuba) by Fernanez Yero and colleagues, consisting of a fast reading vertical spectrophometer-fluorimeter with automated operation and interpretation of results, and the 96-position multipipettes, which enable evaluation of thousands of samples in a very short time and facilitates mathematical processing. This system was calibrated in order to evaluate antibody response in the various vaccine experiments.

Bactericidal microassay.

Slightly modified bactericidal microassay of Frasch and Robbins (*J. Exp. Med.* 147: 229–244; 1978), with improvement of the source of complement by obtaining it from SPF rabbit sera (produced at the Centro de Produccion de Animales de Laboratorio, Habana, Cuba) for assaying sera from immunized mice; and from fresh blood bank donations, when assaying human or monkey sera.

Statistical analysis.

Non-parametric methods were used in the statistical analysis is distributions of ELISA and bactericidal values did not have a normal pattern, but had some asymmetry. The Wilcoxon test for independent sample was mainly used. To obtain a better analysis a wide series of percentiles was calculated thus using another approach to the median of each studied group.

Animal tests.

Tests in mice.

Each variant of the vaccine preparation was submitted to immunogenicity and bactericidal tests in mice (besides the above mentioned safety tests in guinea pigs and mice). The results showed that the preparations are immunogenic and can evoke significant levels of bactericidal antibodies.

Tests in monkeys.

Vaccine variants that were to be used in human volunteers were also tried in monkeys (Macaccus aethipiens) in various doses and schedules. The results showed that they were innocuous, immunogenic, and highly capable of eliciting bactericidal antibodies when compared with the placebo.

Tests in humans.

Reactogenicity tests were carried out in groups of 3, 10 and 30 persons to cover the various doses that were to be assayed; then larger groups were used for immunogenicity tests.

The first groups were closely observed by specialized medical personnel during the initial days, studies included: a) vital signs (pulse, temperature, blood pressure); b) local reactions; c) systemic reactions; d) renal function; e) liver function; f) hematologic study (differential count, platelets, coagulograms); g) higher nervous function (EEG); h) cardiac function (ECG).

None of the studies revealed any pathologic changes in any organ or system with any of the doses studied: ranging from 20 to 100 mcg of protein antigens and the other corresponding components.

The only reactions observed in most of the volunteers were:

1. Slight pain at the injection site, especially during the first 48 hours.
2. Reddening of the injection site and surrounding area.
3. Low fever, with a mean of 37.5° C.
4. Malaise and headache only in a few subjects, very transitory, within the first 10–12 hours.

No serious or remarkable reactions occurred, no immediate or delayed hypersensitivity was observed.

The blood count was slightly changed for neutrophiles and significantly for lymphocytes.

Each volunteer was given a printed form to be filled with their observations. A part of the printed form was to be filled by the medical personnel. This practice has been maintained for the reactogenicity test of each batch produced and released for use.

Immunogenicity tests and induction of bactericidal antibodies in human subjects.

Dose-response studies were carried out in human groups of 100, 200, 300, 500 and 1000 volunteer adults (20–100 mcg) and for determination of vaccination schedules, dose intervals and number of doses. Tests were conducted first in young adults and then with controlled groups of different ages and social background in numbers that gradually increased (3, 10, 30 and 50 subjects).

A. Adults aged 18 to 45 years.
B. Students of both sexes and different educational systems (boarding and non-boarding students) aged 13 to 18.
C. Primary school children aged 6 to 12.
D. Children aged 2 to 6 years.
E. Infants aged 6 months to 2 years.
F. Infants aged 3 to 6 months.
G. Adults aged over 45 years.

Subjects under 12 years of age did not receive doses over 50 mcg. The results were highly satisfactory. No undesirable reactions were observed except for those mentioned. In children those reactions were less intense as age decreased.

Doses of 20 to 100 mcg proved significantly immunogenic, but the best results were obtained with 50 mcg. This dose was selected for all ages with the already described variant, which reached field evaluation. All these studies, including those with animals, reactogenicity, etc. were compared with control groups which were given placebo, having the same appearance, but lacking the active components, that is, aluminum hydroxide only.

Antibody measurements by ELISA and bactericidal tests were made as already mentioned (vide supra.

The responses of various antibody types and subtypes were studied, the most consistently important response being that of Ig G (immunoglobulin G).

For the protection field trial use was made of the variants with the already stated characteristics (less than 10% LPS, 50 mcg protein, 50 mcg polysaccharide C adjuvated with 2 mg aluminum hydroxide). The other variants are being studied in even smaller groups.

Schedules of vaccination selected for the field trial.

Although other schedules using 2 and 5 doses and different intervals are being studied, the one selected was two separate doses with an interval of 6–8 weeks.

Study of hyperimmune gammaglobulin obtained from vaccinated volunteers.

Purification of the plasma Ig G fraction was undertaken using the modified method of E. J. Cohn et al. (*J. Am. Chem. Soc.* 68: 459–476, 1946) from blood donations of 250–350 ml, the extractions having been made more than 4 weeks after vaccination, checking the quality of individual responses (ELISA and bactericidal microassay). The Ig G fraction thus obtained with over 90% purity was submitted to all controls oriented by WHO concerning the use of endovenous preparations (*W.H.O. Tech. ReP. Ser.* 567, 1975, idem. 610, 1977), including tests for AIDS and hepatitis viruses and the confirmation of its content of specific and bactericidal antibodies against the circulating strains. The process considerably enhanced the specific antimeningococcal activity of the preparation as compared with the initial sera. It showed high concentration of specific antibodies against the various antigens of the vaccine preparation and of the native strains and high bactericidal titers against these. Following the scientific and legal procedures its use was sanctioned for children with meningitis and/or meningococcaemia, its use having proved highly effective; its antipyretic effect and its influence in the general state and evolution of patients are specially remarkable. This hyperimmune gammaglobulin is now being produced on a higher scale for distribution to intensive care units throughout the country.

The action of this preparation is due not only to its bactericidal characteristics but also to the possibility of removing various antigens released by lysis from meningococci and whole meningococci (Campa, C. and Sierra, G., *Rev. Ciencia* 2, Julio, 1988; Galguera, M. et al., *Rev. Cub. Hemat. Immun. Hemot.* 2, 1988).

The effect of this hyperimmune antimeningococcic gammaglobulin obtained from vaccinees in the treatment of patients with meningitis or meningococcemia caused by B meningococci is another indirect proof of the vaccine affectivity.

Other results with the vaccine variant sterilized by cobalt 60 ionizing radiations.

An extensive physico-chemical and immunologic characterization of the irradiated preparation was carried out, including studies of teratogenicity, carcinogenicity, mutagenicity, determination of new compounds, and repetition of all the obligatory tests in animals and human volunteers for reactogenicity and immunogenicity.

Finally, the batches of the selected variant with all the control passed satisfactorily were used in a group of 50 young adult volunteers to obtain and evaluate hyperimmune gammaglobulin, which was produced, resulting of the same quality in all its parameters and clinical use to the one obtained from the variant vaccines used in the effectiveness field trial.

Effectiveness field test.

A number of variants of our wide range vaccine are being tested in variants stages in human test. The most advanced variant among these is the one selected for the field trial.

Main characteristics of the vaccine used in the field trial.

1. Protein antigen: 60–75%; majority serotype proteins 12–18%; high molecular weight antigenic complex, 65–95 kD.

Rest; low and high molecular weight contaminants.

2. Polysaccharide C: 50 mcg per dose.
3. Al(OH)$_3$ gel: 2 mg Al(OH)$_3$ per dose; lower than 1.25 mg Al per dose.
4. pH: 7.0±0.4
5. Gel adsorption: Higher than 80% for the vaccine antigens.
6. LPS: Lower than 10%.
7. Polysaccharide B: Lower than 5%.
8. Nucleic acid: Lower than 10%.
9. Thiomersal: 0.005 to 0.02%.
10. Stability: Over 2 years at 2°–8° C.

Immunobiologic characteristics.

1. The presence of the high molecular weight antigenic complex, with bands common to all B serotypes tested, and the final arrangement of all these antigens on the vesicle of majority proteins and LPS confer the property of eliciting antibodies not only against the serotype from which the majority proteins were extracted, but also against quite different strains which have in common only some antigen of the high molecular weight complex.

EXAMPLES:

| Strain/Type | | | Bactericidal titer |
| --- | --- | --- | --- |
| Cuba 385 | B4 | P1:15 | 1/64–1/256 |
| Norway 44/76 | B15 | P1:16 | 1/32–1/256 |
| USA B2 | | | 1/32–1/128 |

2. Four to six months after the second dose there was a sensitive drop of the antibodies to the majority proteins by ELISA and Bactericidal Assay; the antibodies to the high molecular weight antigen complex remain. This was verified by using vaccine variants with different compositions and Western-Blotting studies.

3. Stability of the vesicular complex and its immunogenicity as well as its immunologic memory were increased as high molecular weight component was increased.

Two effectiveness trials were carried out in the field

A. Mass vaccination of the highest risk population aged 6 months to 24 years in a whole province was conducted. The province with the highest historical incidence, a 30 per 100,000 rate, was selected; and 145,000 persons were vaccinated. No other type of vaccine or placebo was used in this study; several studies are being made on different social and age groups, the results of which will be compared with the historical incidence and the non-vaccinated population. The graph shows the initial months of the campaign and the behavior of the disease. The legend of the drawing states that the heavy line graph depicts the incidence during vaccination and the lighter line graphs depict the historical behavior of the disease. The number of cases was plotted against the period of time from the beginning of vaccinations in 1987 to the end of the vaccinations in 1988. As can be seen, the epidemic has been cut down in that province and now comparing the total number of cases in each province, where one can observe that the one with the highest rate in the past is not so any more.

B. The principal trial, according to the requirements for the approval of new vaccines, is a placebo-vaccine double-blind trial including a total 106,000 boarding students in 7 high incidence provinces. The populations receiving either vaccine or placebo were larger than necessary so that after more than one year—which is the time since the beginning of the experience—the normal losses in such large and mobile populations as boarding students the required figures should be available.

For further details on the planning of this study of effectiveness in the field, reference is made to an official document issued by Bureau of Epidemiology of the Cuban Ministry of Public Health, "Estudio de campo de la vacuna antimeningococcica de proteina de membrana externa y polisacarido C", 14 Nov. 1986, Havana.

Results of the first evaluation of the double-blind PLACEBO—VACCINE experiment.

The seroconversion levels by ELISA and Bactericidal Test and the results of the therapeutic use of the hyperimmune Gamma Globulin obtained from the vaccinees, including the incidence during the field trials (see the FIGURE) show the superior effectiveness of the new generation of vaccine over historical results.

EVALUATION RESULTS

| Group | Total to date | Seroconversion (%) | |
|---|---|---|---|
| | | ELISA | BACTERICIDAL TEST |
| Vaccinees | 52,966 | 90 | 70 |
| Placebo | 53,285 | 14 | 12 |
| Total | 106,251 | | |

The correlation of the carrier state before vaccination was analyzed as a possible coincidential factor with null or atypical responses to the vaccine. Both the above results and those of the application of the antimeningococcal hyperimmune gamma globulin allow one to predict that we have a generation of group B antimeningococcal vaccine, which is superior to previous ones and for the first time effective and capable of being scaled-up.

The initial strain in the present invention may in principle be any pathogenic strain of B meningococci circulating or responsible for the majority of the disease in the region where vaccine protection is sought. This strain is adequately characterized, especially as refers to stability and growth requirements in selected culture media.

The microorganism is adequately cultivated and centrifuged to obtain 500 g (wet weight) of biomass of group B *Neisseria meningitidis*, which is resuspended in 2500 ml of a sodium deoxycholate (0.09% sodium deoxycholate, 50 mM Tris-HCl pH =8.5, 2 mM EDTA) to which 0.05% lysozyme is added. The extraction process is carried out during 2 ½ hours at 4° C., during which period of time 10 treatment courses of 30 second ultrasonic baths are given, alternating with magnetic stirring at 250 rpm.

The cell debris is separated from the extract by centrifugation at 10,000 g. The supernatant is treated with DNase and RNase at a concentration of 5 mg per extract liter each at 37° C.

The extract is centrifuged at 100,000 g during 2 hours, the sediment is suspended in 200 ml 5% deoxycholate buffer in Tris-EDTA, pH 8–9. Chromatography is performed by molecular sieving in a matrix of SEPHACRYL S-300 with 1% deoxycholate buffer for elution purposes. The first peak is collected and monitored on the UVICORD spectrophotometer at 280 nm.

The first peak eluted from this fractioning is the basic material containing the vesicles, to which the high molecular weight antigenic complex is added in a proportion of 12–18%. This complex is extracted by enrichment of the fraction of 65–95 kD from the first peak by repeating the ultrasonic treatment in presence of 5% Tris-EDTA deoxycholate buffer, followed by an affinity chromatography in a column with anti- P1 and anti-P3 monoclonal antibodies, concentration by ultrafiltration and final chromatography on a preparative column (TSK 300-SWG) with Tris-EDTA buffer.

The protein preparation which contains 60–75% of serotype proteins and 12–18% of high molecular weight antigenic complex, is precipitated and washed in ethanol, after previous sterile filtration on Sartorius type membrane. Maintaining the sterility conditions capsular polysaccharide is added in a 1: 1 polysaccharide-protein proportion. This group C polysaccharide was produced according to Gold et al., 1969–1970, *WHO Bull.* 45: 279–282 and Gotschlich et al., 1969, *J. Exp. Med.* 129: 1349–1365) and sterilized by membrane filtration (vide supra).

Finally, to the protein-polysaccharide mixture aluminum hydroxide is added as adjuvant in a proportion of 2 mg of Al $(OH)_3$ for each 50 mcg of protein and polysaccharide, amounts representing the contents of one dose. The adjuvant gel is previously radiosterilized using cobalt 60 irradiation with a dose of 15 kGy at a temperature of 4° C.

A final pH of the preparation of 7.0±0.4, an adsorption to the gel of more than 80% of the total protein and polysaccharide, and a content of 10% LPS are guaranteed.

As preservative thimerosal is used at a concentration of 0.005–0.02%.

The whole product is subjected to a battery of physicochemical and biological controls described in the patent.

It is understood that the description and examples as well as embodiments described herein are for illustrative purposes only and that various modifications or changes in light thereof will be suggested to persons skilled in the art and are to be included within the spirit and purview of this application and the scope of the appended claims.

What is claimed is:

1. A method for producing antimeningococcic hyperimmune gamma-globulin which comprises:

1) vaccinating an adult with a vaccine against *Neisseria meningitidis* B pathogens prepared by the method steps performed in the following order of:

a) extracting the vesicles of the outer membrane and protein antigenic complex weighing from 65 to 95 kD from live, active pathogens of group B serotypes with a treatment selected from the group consisting of:

(i) treating with detergent, (ii) treating with detergent and ultrasound, and (iii) treating with detergent, enzymatic solution and ultrasound to create an extract;

b) treating said extract to eliminate nucleic acids to create a treated extract;

c) purifying said treated extract to separate as a fraction the said vesicles from the protein antigenic complex by a dissociative treatment with detergent solution, ultrasound, and column chromatography to produce purified protein antigenic complex;

d) further purifying said purified protein antigenic complex by a chromatographic step from the group consisting of high performance liquid chromatography, affinity chromatography with monoclonal antibodies, hydrophobic chromatography, and ionic exchange chromatography, and combinations thereof, to obtain a further purified protein antigenic complex;

e) combining said further purified protein antigenic complex with a fraction containing the vesicles by ultrasound treatment to anchor said further purified protein antigenic complex and vesicles to each other in an effective amount in a proportion of 15%±3% by weight to create an anchored protein complex; and, f) adding capsular polysaccharide and adjuvant to anchored protein complex of step (e), wherein the adjuvant is selected from the group consisting of aluminum hydroxide, aluminum phosphate, and calcium phosphate; and g) recovering the resultant vaccine;

2) drawing blood from the vaccinated adult;

3) separating from the blood drawn from the vaccinated adult of step 2) the antimeningococcic hyperimmune gamma-globulin plasma fraction from other compnents of the blood; the 4) purifying the plasma fraction to isolate to the antimeningococcic hyperimmune gamma-globulin.

2. The method of claim 1 further comprising the step of sterilizing the vaccine by radiation of the individual components or resultant vaccine by cobalt 60 at a dose from 5 to 25 Kilograys at a temperature from 1° to 4° C.

3. The method of claim 1, wherein for the extraction step (a) said detergent is selected from the group consisting of:

(i) deoxycholate from 0 to 0. 1% wgt/vol, (ii) sodium dodecyl sulfate from 0.1% to 5% wgt/vol, (iii) polyoxyethylene 10, oleyl ether from 0.01 to 0.5% wgt/vol, (iv) sorbitan monooleate polyoxyethylene from 0.1 to 2% wgt/vol, and (v) mixtures thereof, and the enzyme is lysozyme at a concentration from about 0.03 to about 1% wgt/vol.

4. The method of claim 1, wherein the extraction step (a) is carried out at 2°–10° C. for 5 minutes to 5 hours in a medium buffered at a pH of 6.5 to 9, with stirring at 250 to 950 rpm.

5. The method of claim 1, wherein for purifying said treated extract of step (c) the detergent is selected from the group consisting of sodium deoxycholate, polyoxyethylene 10, oleyl ether, sorbitan monolaurate polyoxyethylene, and sorbitan monooleate polyoxyethylene, wherein the detergent is at a concentration of 0.1 to 6% wgt/vol., the column chromatography comprises a matrix selected from the group consisting of a cross-linked copolymer of allyl dextran and N,N'-methylene bis acrylamide for fractionation of globular proteins with a molecular weight range of 10,000–1.5 million, a cross-linked copolymer of allyl dextran and N,N'-methylene bis acrylamide for fractionation of globular proteins with a molecular weight range of 20,000–8 million, and a cross-linked beaded agarose for fractionation of globular proteins with a molecular weight range of 60,000–20 million.

6. The method of claim 1, wherein the anchored protein complex of step (e), the capsular polysaccharide of step (f), and the adjuvant of step (f) are each individually sterilized further by a sterilization procedure selected from the group consisting of membrane ultrafiltration and radiosterilization and combinations thereof.

7. The method of claim 1, wherein the pathogens of step (a) are from the concentrate of a supernatant of the culture.

8. The method of claim 1, wherein the capsular polysaccharide is added in a ratio of 1.1 to 1.4 by weight with respect to said anchored protein complex of step (e), and said adjuvant is added in a ratio of 20–100 by weight with respect to said anchored protein complex of step (e).

9. The purified and isolated meningococcic, hyperimmune gamma-globulin produced by the process of claim 1.

10. The purified and isolated antimeningococcic, hyperimmune gamma-globulin of claim 9, wherein the gamma-globulin is immunoglobulin G.

* * * * *